United States Patent
Roberts et al.

(10) Patent No.: US 9,901,515 B2
(45) Date of Patent: Feb. 27, 2018

(54) SMART CAP FOR MEDICATION CONTAINER

(71) Applicant: Performance Designed Products LLC, Burbank, CA (US)

(72) Inventors: Tom Roberts, Alpine, CA (US); Chris Richards, Fountain Hills, AZ (US); Steve Lavache, Ware (GB); Ireck Briones, Spring Valley, CA (US); Mario Andres Quiros, Del Rey, CA (US)

(73) Assignee: Perfomance Designed Products LLC, Burbank, CA (US)

( * ) Notice: Subject to any disclaimer, the term of this patent is extended or adjusted under 35 U.S.C. 154(b) by 0 days.

(21) Appl. No.: 15/148,383

(22) Filed: May 6, 2016

(65) Prior Publication Data

US 2016/0324726 A1    Nov. 10, 2016

Related U.S. Application Data

(60) Provisional application No. 62/158,378, filed on May 7, 2015.

(51) Int. Cl.
*A61J 7/04*      (2006.01)
*B65D 51/24*     (2006.01)
(Continued)

(52) U.S. Cl.
CPC ........... *A61J 7/0418* (2015.05); *A61J 7/0076* (2013.01); *A61J 7/02* (2013.01); *A61J 7/04* (2013.01);
(Continued)

(58) Field of Classification Search
CPC A61J 2200/30; A61J 2200/74; G06F 19/3462
See application file for complete search history.

(56) References Cited

U.S. PATENT DOCUMENTS

| | | | |
|---|---|---|---|
| 4,674,652 A | 6/1987 | Aten et al. | |
| 4,695,954 A | 9/1987 | Rose et al. | |
| (Continued) | | | |

FOREIGN PATENT DOCUMENTS

| | | |
|---|---|---|
| WO | WO2012102759 A1 | 8/2012 |
| WO | 2013/127564 A1 | 9/2013 |

OTHER PUBLICATIONS

IMC, eCAP, Retrieved from: http://www.informationmediary.com/ecap, Mar. 28, 2014, p. 1.
(Continued)

*Primary Examiner* — Timothy Waggoner
(74) *Attorney, Agent, or Firm* — Sheppard Mullin; Daniel Yannuzzi; Jonathan Marina

(57) ABSTRACT

A smart cap for a medication container is disclosed. The smart cap includes a circuit board and a weight sensor electrically coupled to the circuit board and configured to generate electrical input signals representative of the total weight of medication units in the medication container. The smart cap may include a processor for processing the electrical input signals generated by the weight sensor, and a memory for storing medication information associated with medication in the medication container, including the processed electrical input signals generated by the weight sensor. The smart cap may transmit the stored information to a computing device communicatively coupled to the cap.

19 Claims, 9 Drawing Sheets

(51) Int. Cl.

| | | |
|---|---|---|
| *B65D 55/02* | (2006.01) | |
| *A61J 7/02* | (2006.01) | |
| *G01G 3/14* | (2006.01) | |
| *G01G 19/52* | (2006.01) | |
| *A61J 7/00* | (2006.01) | |
| *G06F 19/00* | (2018.01) | |
| *A61J 1/14* | (2006.01) | |

(52) U.S. Cl.
CPC ........... *A61J 7/0436* (2015.05); *A61J 7/0463* (2015.05); *B65D 51/248* (2013.01); *B65D 55/02* (2013.01); *G01G 3/1402* (2013.01); *G01G 19/52* (2013.01); *G06F 19/3462* (2013.01); *A61J 1/1412* (2013.01); *A61J 1/1437* (2013.01); *A61J 2200/30* (2013.01); *A61J 2200/74* (2013.01)

(56) References Cited

U.S. PATENT DOCUMENTS

| | | | |
|---|---|---|---|
| 5,014,798 A * | 5/1991 | Glynn | G01G 11/006 177/132 |
| 7,269,476 B2 | 9/2007 | Ratnakar | |
| 7,369,919 B2 | 5/2008 | Vonk et al. | |
| 7,801,745 B2 | 9/2010 | Walker et al. | |
| 8,319,613 B2 | 11/2012 | Lazar | |
| 8,751,039 B1 * | 6/2014 | Macoviak | A61J 7/0076 700/236 |
| 2006/0152364 A1 | 7/2006 | Walton | |
| 2006/0217014 A1 * | 9/2006 | Pierce, Jr. | B63C 9/26 441/123 |
| 2007/0016443 A1 | 1/2007 | Wachman | |
| 2007/0299687 A1 | 12/2007 | Palmer et al. | |
| 2008/0027291 A1 | 1/2008 | Williams-Hartman | |
| 2008/0117719 A1 * | 5/2008 | Hildebrandt | A61J 7/0472 368/10 |
| 2009/0043253 A1 | 2/2009 | Podaima | |
| 2009/0299522 A1 | 12/2009 | Savir et al. | |
| 2010/0164716 A1 * | 7/2010 | Estevez | G06F 19/3462 340/540 |
| 2011/0112686 A1 | 5/2011 | Nolan et al. | |
| 2011/0169635 A1 | 7/2011 | Johnson | |
| 2012/0003928 A1 * | 1/2012 | Geboers | A61J 7/0084 455/41.1 |
| 2012/0239419 A1 | 9/2012 | Allen | |
| 2014/0188502 A1 * | 7/2014 | Defrank | G06F 19/3462 705/2 |
| 2014/0266760 A1 * | 9/2014 | Burke, Jr. | G06F 19/3462 340/687 |
| 2014/0350720 A1 | 11/2014 | Lehmann et al. | |
| 2015/0272825 A1 * | 10/2015 | Lim | A61J 1/03 340/5.2 |
| 2016/0058661 A1 * | 3/2016 | Pether | A61J 7/0084 455/557 |

OTHER PUBLICATIONS

Connolly, Kate. Smarty Packs, Retrieved from: http://fused180.com/wp-content/uploads/2013/04/Published-Smarty-Packs-364715.pdf, Feb. 26, 2013, pp. 1-5.

International Search Report and Written Opinion for corresponding International Application PCT/US2016/031302 filed May 10, 2016.

\* cited by examiner

SMART CAP FOR MEDICATION CONTAINER

CROSS-REFERENCE TO RELATED APPLICATIONS

This application claims the benefit of U.S. Provisional Patent Application No. 62/158,378 filed May 7, 2015 and titled "Smart Cap For Medication Container", which is incorporated herein by reference in its entirety.

TECHNICAL FIELD

The present disclosure relates generally to smart caps for medication containers, and more particularly, some embodiments relate to smart cap systems and methods for a medication container.

BACKGROUND

Low prescription medication adherence is a major problem in the United States with annual costs of over 200 billion dollars. Although several products have been marketed for improving adherence, the majority are too costly for most patients. Examples of such products are described below.

GlowCap® is a universal bottle cap that provides a series of escalating audio and visual alerts to remind patients to take their medication. The GlowCap® syncs directly through a mobile broadband network using a local hub. If a patient forgets to take a prescribed medication, he or she may be sent a text message through the mobile network. The GlowCap® has limited mobility as it only works in the presence of a mobile network a hub, and is carrier specific. Additionally, it needs its own data connection and is costly.

The MedMinder™ pillbox is a 28 compartment pillbox with an internal cellular modem. The pillbox compartments may be prefilled by pharmacies. The box provides audio, visual, text message, and email reminders to take medications, and the internal cellular modem communicates with a remote system for medication refill and tracking. Its main shortcoming is the high monthly fee needed to support its cellular data connection.

CleverCap® is a universal bottle cap that is programmed to time release tablets. Audio, visual, and mobile reminders may be delivered. The main short shortcomings of CleverCap® are its large size, price, and lack of scale.

PharmAssistant is a smart pill container equipped with a Bluetooth radio that communicates with a patient's smartphone through an app. During operation, the smart pill container must be in proximity to the smartphone, which, through the app, causes the box to provide audio and visual reminders to take medication until the box is opened.

SUMMARY

In various embodiments of the disclosed technology, a smart cap for medication containers is described. In one embodiment, the smart cap includes a circuit board; a weight sensor electrically coupled to the circuit board and configured to generate electrical input signals representative of a total weight of medication units in the medication container; a processor electrically coupled to the circuit board and configured to process the electrical input signals generated by the weight sensor; a memory configured to store medication information associated with medication in the medication container, where the medication information includes the processed electrical input signals generated by the weight sensor; and a wireless transmitter configured to transmit the stored medication information to a computing device communicatively coupled to the smart cap.

In implementations of this embodiment, the wireless transmitter may be a Bluetooth low energy (LE) transmitter or an RFID tag that also includes a memory for storing medication information. In embodiments, the RFID tag may be an NFC tag. The cap may include a lock that is unlockable when a computing device is brought in close proximity (e.g., less than 20 cm) to the NFC tag of the cap.

In additional implementations of this embodiment, the cap includes an audible or visual indicator device configured to alert a user of a medication dosing time, and the processor is configured to activate the indicator device at the dosing time. In these implementations, the indicator device may also help a user locate the medication container the smart cap is attached to. The transmitter may be a transceiver that receives information signals from the computing device, and in response to receiving a beacon signal from a computing device attempting to locate the cap, the processor may activate the indicator device.

In particular implementations, the processor is configured to: determine a change in the total weight of the medication units in the medication container after the dosing time based on electrical signals generated by the weight sensor; and turn off the indicator if it is determined that the change in the total weight after the dosing time matches a predetermined amount. The processor may generate an alert if it is determined that the change in the total weight does not match the predetermined amount.

In further embodiments, in response to a computing device communicatively coupling to the cap, the processor is configured to store in the memory an identification of the computing device, and the time the cap and computing device communicatively coupled.

In another embodiment, the smart cap includes: a circuit board; a weight sensor assembly electrically coupled to the circuit board and configured to generate electrical input signals representative of the total weight of the medication container; a cover; and an enclosure attached to the cover. The enclosure is disposed within the cover and is configured to seal the opening of the medication container and house the circuit board and weight sensor assembly. In this embodiment, the cap may additionally include an accelerometer configured to generate electrical input signals representative of the position of the cap.

In further embodiments of the disclosed technology, a weight sensor assembly that may be used in the disclosed smart cap is described. The weight sensor assembly includes a platform and load cell. In various implementations, the load cell includes an annular portion and one or more beams extending inwardly from the annular portion and coupled to the platform. The beams include a first end fixed to the annular portion; and a second end that deforms as the platform displaces downward in response to an applied force. In embodiments, one or more strain gauges may be attached to the beams. For example, one strain gauge in compression and one strain gauge in tension may be attached to the beams.

In various implementations, the diameter of the load cell (i.e., outer diameter of the annular portion) is at least 100 times greater than the thickness of the load cell. In a particular implementation, the diameter of the load cell is between 30 and 45 millimeters, and each of the first beam and the second beam is between 0.2 and 0.3 millimeters thick and between 3.5 and 5.5 millimeters wide.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The technology disclosed herein, in accordance with one or more embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION

The technology disclosed herein is directed toward a smart cap for medication containers. Some embodiments are directed toward a universal smart cap that may be fitted on standard, easy-open and childproof medication containers. In various embodiments, the disclosed smart cap wirelessly transmits medication-related information to a computing device for further processing, thereby leveraging the computing device's processing power. In various embodiments, this reduces the computing power needed in the cap and enables a low-cost, portable solution for medication tracking and compliance. In further embodiments, a weight sensor assembly with a strain gauge load cell that may be used in the smart cap is described.

Figure 1:
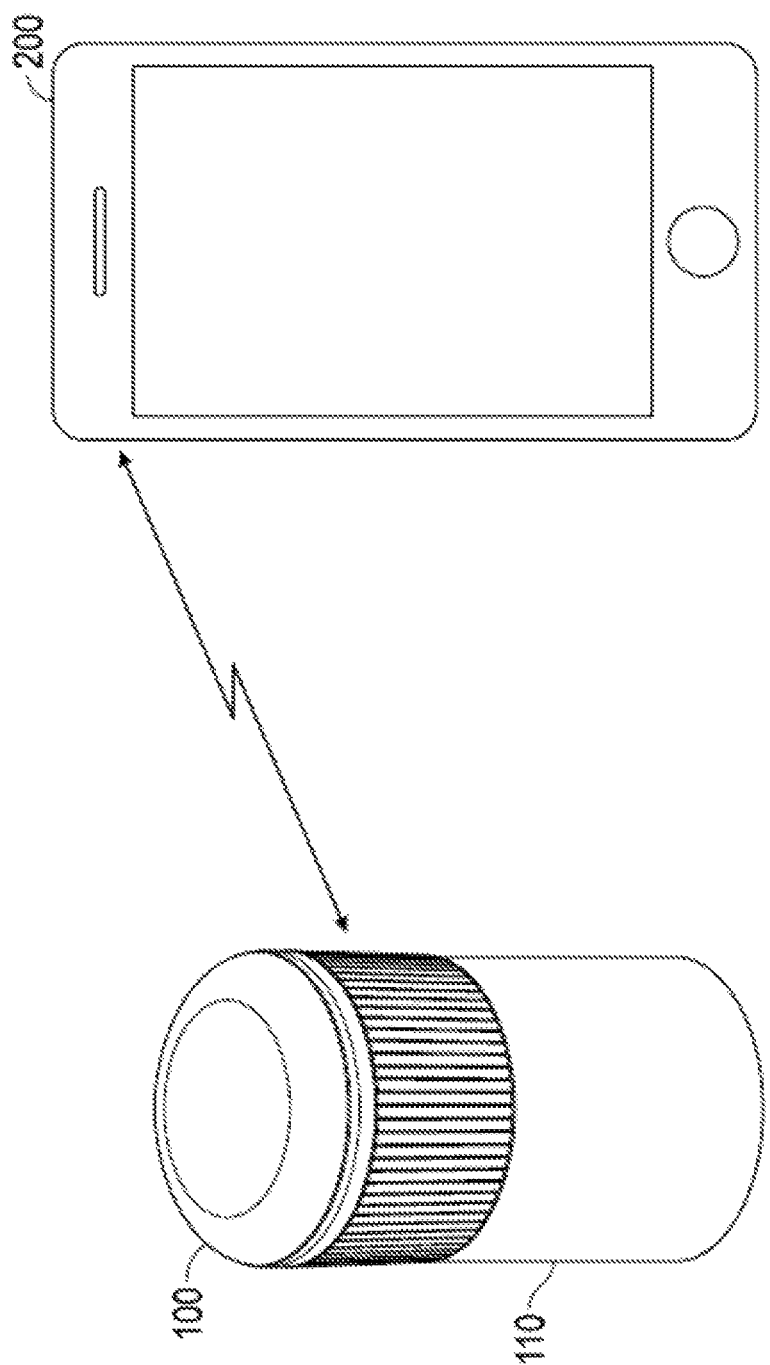
FIG. 1 illustrates an example wireless communications environment in which the disclosed smart cap may be implemented.

FIG. 1 illustrates an example wireless communications environment in accordance with an exemplary embodiment. In this environment, a smart cap 100 attached to medication container 110 communicates with a computing device 200 over a wireless communication link. Although a smartphone is illustrated, computing device 200 may comprise any computing device (smartphone, tablet, laptop, smartwatch, desktop, etc.) configured to receive medication-related information from smart cap 100, and one or more processors and memory modules for processing and interacting with the data collected by smart cap 100. Computing device 200 may also provide a graphical user interface (GUI) to perform functions such as accepting user input and displaying information to the user.

Information displayed to the user can include, for example, information about the prescription associated with the smart cap (e.g., contained in the container used with the smart cap). This information can include information such as prescribed dosage times, quantities (e.g. number of pills) and amounts (e.g. milligrams of the dose), whether the patient is current with his or her dosing interval, whether the patient is behind in a dosing interval, the patient's history of taking the medications as tracked by the smart cap, doses remaining in the container, refill dates and statuses, and so on. This information can also include general information about the prescription such as, for example, information about the prescription, side effects, dosing instructions (e.g. take with meals), medication warnings, drug interaction precautions, and so on.

Input that can be accepted on the GUI can include inputs such as, for example, input by the user querying for information on prescription and dosing history, manual input by the user confirming that particular dose was taken or confirming that a dose was intentionally skipped, and other like information the user may enter regarding the prescription in a dosing. Additionally, the GUI may provide the user with input to order refills, communicate with his or her health care provider, query the system for information about the prescription, and so on.

In preferred embodiments, the wireless communication link is a low energy communication link such as a radio frequency link based on near field communications (NFC), a Bluetooth low energy (LE) link, or a ZigBee link. However, in alternative embodiments other wireless communication methods may be used, including those known in the art such as WiFi, mobile data, and others. In still further embodiments, a wired communication link can be provided between the smart cap 100 and computing device 200.

Figure 2A:
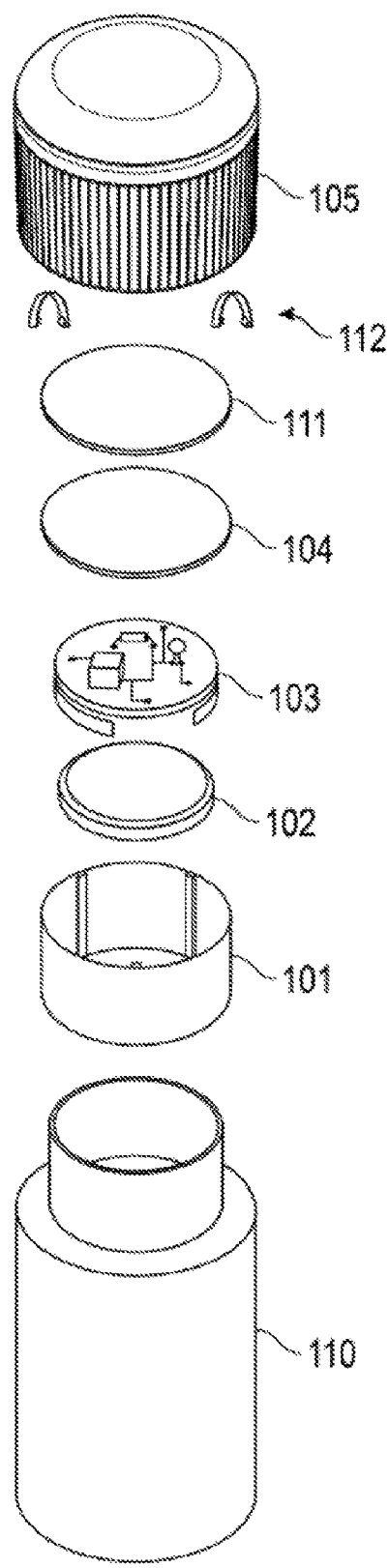
FIG. 2A is a diagram illustrating components of a smart cap in accordance with an example embodiment of the disclosed technology.

FIG. 2A is a diagram illustrating components of a smart cap 100 in accordance with an example embodiment. Particularly, this example illustrates an exploded view of an example smart cap 100. As illustrated in this example, smart cap 100 includes an enclosure 101 for sealing the opening of medication container 110, a battery 102, circuitry 103, a weight sensor 104, a cap 111, and a cover 105.

As shown, enclosure 101 in this example is configured to provide a housing for battery 102, circuitry 103 and weight sensor 104. When mated with cap 111, the combination of enclosure 101 and cover 105 can provide a secure and even moisture-proof housing for the components contained therein. Depending on the application, the housing can be configured to provide a watertight seal or even a hermetic seal for the components contained therein.

As shown in this example, enclosure 101 can be configured to be disposed within cover 105. In some embodiments, container 101 is dimensioned such that it does not contact the lip of medication container 110. In other embodiments, it may contact medication container 110. In still further embodiments, enclosure 101 may be dimensioned having a diameter such that it fits within the mouth of medication container 110.

Spring tabs 112 can be included to releasably mate enclosure 101 and the components contained therein to cover 105. Although spring tabs 112 are illustrated as the attachment mechanism, other attachment devices can be used including, for example, threads or locking tabs. The use of a releasable mating mechanism such as spring tabs 112 allows enclosure 101 to be removed from cover 105 to allow access to the components contained therein. This can be used, for example, to replace battery 102 or any of the other components, to electrically connect to the circuitry 103 via a wired port, or to otherwise access the contents of enclosure 101.

Although not illustrated in the figure, enclosure 101 can include threads, tabs or other attachment mechanisms to allow enclosure 101 to be releasably attached to medication container 110. In other embodiments, cover 105 can be configured with threads, tabs, or the other attachment mechanisms to allow the cap to be releasably attached to medication container 110.

Circuitry 103 may include components used to perform the features and functions described herein including, for example a microcontroller or other processing system (e.g., having one or more processors or processor cores and suitable memory) program to perform these described functions and other functions as would be apparent to one of ordinary skill in the art upon reading this description.

Figure 2B:
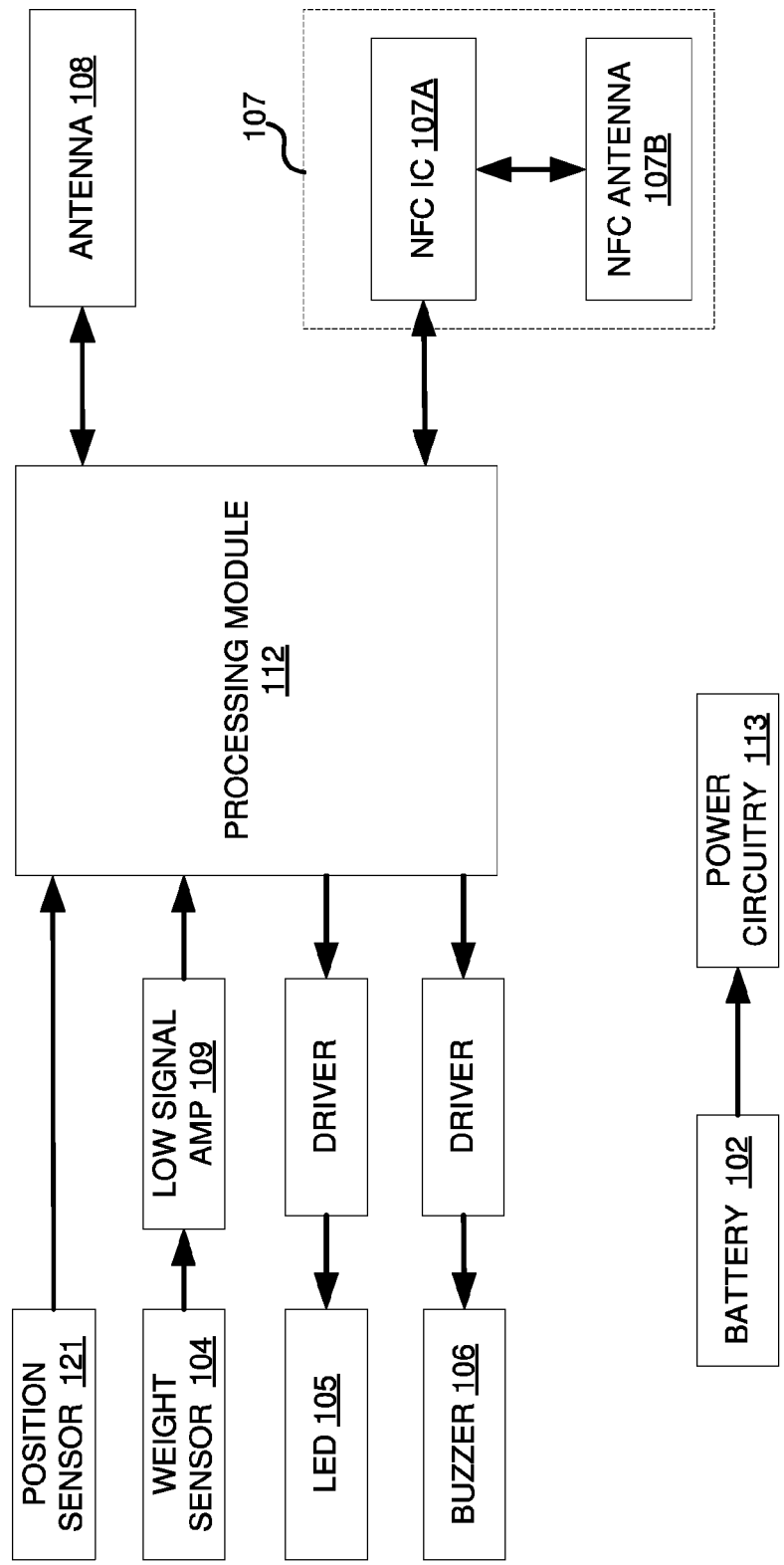
FIG. 2B is a block diagram illustrating an example architecture for the circuitry of the smart cap of FIG. 2A.

FIG. 2B is a diagram illustrating an example architecture for such circuitry in accordance with one embodiment of the technology disclosed herein. In this example, circuitry includes a processing module 112, which in this example is a single IC microcontroller, indicator devices 105, 106, and antenna 108, a wireless communication interface 107, and power circuitry 113. FIG. 2B also shows how circuitry 103 interfaces with battery 102, a weight sensor 104 including a low signal amplifier 109, and a position sensor 121.

As noted above, in this example processing module 112 is a microcontroller and can include memory for storing program information and data and interfaces to allow interfaces to the other components of the system. In other embodiments, other processing modules can be used including, for example, ASICs, FPGAs, processor systems using one or more single or multi-core processors, and so on.

As illustrated in this example, interfaces are provided such that processing module 112 can receive weight signals from weight sensor 104 that indicate the weight of the medication container 110 when it is positioned such that the smart cap 100 bears the entire weight of medication container 110. In various embodiments, a position sensor 121 (e.g., an accelerometer and/or gyroscope) may provide position signals to processing module 112 to determine that smart cap 100 is in the correct position while weight sensor 104 takes weight measurements. In a particular implementation, the position sensor 121 is an accelerometer that detects the relative orientation of smart cap 100 based on the acceleration due to gravity.

In embodiments, the weight signals provided by weight sensor 104 can be amplified, if needed, by a signal amplifier 109 to provide the appropriate signal levels to processing module 112. In embodiments, low signal amplifier 109 may be part of weight sensor 104 or circuitry 103.

As described further below, processing module 112 can use the weight information contained in the weight signals to determine the weight of medication container 110. This information can be used to determine the weight of the contents (i.e. the medicaments) in medication container 110. The microcontroller can further be programmed to determine the quantity of medicaments in the medication container 110 based on the computed weight of the contents and information about the medicaments contained in the container such as, for example, medicament and medicament dosage information. In some implementations of these embodiments, processing module 112 may first use the position signals generated by position sensor 121 to verify that smart cap 100 was in a correct position during weight measurement before determining the weight of medication container 110 based on the weight signals.

Information about the medicaments can be preprogrammed by the pharmacy when the medication container 110 is filled. Alternatively, information about the medicaments can be preprogrammed at the factory and the smart cap can be designated for the particular medicaments for which it is programmed. In still further embodiments, information about the medicaments can be programmed by the user such as, for example, by the graphical user interface included with device 200. While in some environments it may not be desirable to allow the user to alter the medicament information, in some applications this can be done to allow the user to repurpose medication container 110 and smart cap 100 for various further uses. Because it may be desirable to minimize power consumption, and accordingly processing power, these computations can be made external to the smart cap 100 such as, for example, by device 200. In such embodiments, the weight signals and position signals, or information contained in the weight signals and position signals, can be transferred to the external device (e.g. device 200) for computation and reporting to the user.

In the illustrated embodiment, the electrical components are powered by a coin cell battery 102. However, other suitable battery or power supply technologies known in the art or later developed may be used. For example, piezo or vibration energy harvesters, photovoltaic cells, or other like devices can be used. In some embodiments, the circuitry can be configured to remain on at all times such that alerts can be generated, measurements made, and other activities occur in real time as may be needed depending on the device program. In other embodiments, circuitry can be configured to enter a low-power or sleep mode such that various of the components enter a low-power or inactive mode when the device is not in use. For example, processing module 112 can be configured to maintain a timer and "wake up" at certain times or at periodic intervals to measure the quantity of medicaments in the container and to report back to device 200 or to other external systems. In still further embodiments, mechanisms such as, for example, an on/off switch can be provided to allow the user to manually control the on/off state of the device. In even further embodiments, devices such as micro switches or gravity switches can be used to determine when the container is placed with the lid facing down.

In various embodiments, smart cap 100 may include memory, as noted above, to store computing instructions and to store information that can be used by the system (processing module 112, device 200, or both). In some embodiments, sufficient memory is provided to store information about the contents of the container and information obtained from one or more sensors (e.g., weight sensor and position sensor) for transmission to computing device 200 for processing. This information may include, for example, the name of the drug or drugs in medication container 110, the patient's name, an identification of the patient's computing device, the date and time the container was last opened, the total weight of medication units in the container, the current orientation of the medication container 110 and cap 100, and the change in weight of medication units since the container was last opened.

In preferred embodiments, smart cap 100 transmits information to and receives information from computing device 200 using an RFID or Bluetooth LE connection. In one such embodiment, information may be transmitted and optionally received by smart cap 100 using a RFID NFC tag or other NFC device 107. An example NFC device 107 can include single or bidirectional communication for NFC applications and can further be enabled by placing it within close proximity of or touching a compatible NFC or RFID equipped computing device 200. As an example, the information transmitted by smart cap 100 may include the date and time the container was last opened, the current position of smart cap 100, and the change in weight of medication units since the container was last opened. As another example, the information received by smart cap 100 may include updated patient information, updated medication information, or an instruction to unlock the smart cap.

As another example, smart cap 100 can transmit an alert to device 200 if the container remains unopened and the weight of the container has not changed within a predetermined time after a scheduled dosing time. In such an example, processing module 112 can include enough processing power and program instructions to enable processing module 112 to detect the current time, determine the open/close state of the container, determine the weight of the contents in the container, and determine whether the information indicates that the patient failed to take a prescribed dose at the prescribed dosing time. As yet another example, smart cap 100 can transmit an alarm to device 200, based on the signals generated by position sensor 121, if the container is not in a correct position to measure weight.

In other embodiments, processing module 112 can simply gather information about the state of the container (e.g., weight signals, position signals, the open/close state, and other data) and provide this information to device 200 to perform the computation and generate the alarm if necessary. In such embodiments where processing module 112 gathers data and transmits the data to device 200 for processing, as opposed to performing the processing computations itself, circuitry 103 can be implemented at a lower cost and it can consume less power.

In various embodiments, information may be communicated by initiating a handshaking procedure between smart cap 100 and computing device 200 at predetermined times or predetermined periodic intervals (e.g., a few times per day to conserve battery life). In these embodiments, the handshaking procedure may be initiated by smart cap 100 or computing device 200. In further embodiments, smart cap 100 may include a button to mute the handshake function, thereby conserving the battery life of battery 102.

Prior to use, a pharmacist or patient may program the cap with data including a medication identification, patient name, dosage quantities and times, warnings, any special instructions, and other information that may be useful to the patient or to the processing system. In embodiments, further described below, this data may be programmed using a medication tracking application (app) installed on computing device 200.

Also illustrated in the example of FIG. 2B are user alert mechanisms, which in this example include an LED 105 and a buzzer 106. Accordingly, processing module 112 can be configured to trigger an alert via an audible alert mechanism, a tactile alert mechanism, or a visual alert mechanism, or a combination of the foregoing. For example, the system can be configured to provide a particular alert at the dosing time and another alert if the device determines that the patient missed a dose. Further, an alert can be provided before the dosing time to alert the patient that the dosing time is approaching. The alerts can be different to differentiate amongst these different occurrences such as, for example, by using different color LEDs, a different sequence of flashing indicators, different sounds or tones, and so on.

In further embodiments, circuitry 103 can be configured to provide escalating visual and audio reminders to the patient to, for example, warn the patient of an upcoming dosage time, and alert the patient if a dosage time has passed. For example, when it is time to consume medication, LED 105 may flash and buzzer 106 may sound an alarm for a predetermined period of time. After a patient removes smart cap 100 and consumes one or more medication units, smart cap 100 may store the date/time of consumption, the ID of the computing device 200 it last communicated with, and the change in weight of the medication units measured using weight sensor 104. If it is determined (e.g., by processor module 112 or smart device 200) that the patient did not consume the appropriate quantity of medication units, did not consume any medication units at the predetermined time, or did not remove smart cap 100, another alert can be provided.

In embodiments, smart cap 100 may include a locking mechanism that may be unlocked using a medication tracking application installed on computing device 200. For example, device 200 can send an unlock signal to circuitry 103 to unlock smart cap 100, thereby allowing medication container 110 to be opened. In some embodiments, device 200 can be configured to wirelessly transmit an unlock signal (or a lock signal to lock the container) to circuitry 103. In embodiments where the computing device 200 includes NFC capabilities, smart cap 100 may be unlocked by bringing smart cap 100 into close proximity with device 200.

Computing device 200 can be configured to require a password, PIN, or other security code before sending a signal to unlock the container. This can provide a measure of security to the container and may also provide a child-safe container. In embodiments, computing device 200 may interface with multiple containers. In these embodiments, mechanisms may be provided via the medication tracking application to allow the user identify which containers should be opened or unlocked. In further embodiments, the system can be configured to automatically identify the containers to be unlocked based on the dosing times of the medicaments contained in the medication containers. Where multiple users are using device 200 to access their respective medication containers, user IDs can be used to differentiate amongst the users who have access to the particular containers.

In single-user embodiments, smart cap 100 may record the ID of the computing device 200 used to unlock smart cap 100, thereby providing an identification of the person that accessed the medication. In single- or multi-user embodiments, smart cap 100 may record the ID of the user who accessed computing device 200 to unlock smart cap 100.

As noted above, one or more wired or wireless communication interfaces can be included to allow smart cap 100 to interface with device 200. As shown in the example of FIG. 2B, circuitry 103 can include a near field communication device 107 or antenna 108 for non-NFC communications. In the illustrated example, antenna 108 is a surface mount technology (SMT) antenna that can be directly mounted to a printed circuit board on which other components of circuitry 103 are also mounted. Also in the illustrated example, NFC device 107 includes an NFC IC 107A and an NFC antenna 107B.

In one particular embodiment, circuitry 103 may be implemented as an RFID tag that is active or battery-assisted passive. In this embodiment, the RFID tag may include an RF antenna for receiving and transmitting signals, an integrated circuit for storing and processing medication-related information, modulating and demodulating RF signals, and a power source. The RFID tag may include fixed or programmable logic for processing medication-related information. Additionally, the RFID tag storage may be read-write, read-only, or write once, read many (WORM). In implementations where the RFID tag is an active RFID tag, it may broadcast an RF signal including its ID signal and/or medication-related information at predetermined times or predetermined periodic intervals (e.g., a few times per day to conserve battery life).

In another embodiment, circuitry 103 may be implemented as a passive RFID tag without its own power source. For example, the RFID tag may be a near field communication (NFC) tag that is powered by an electromagnetic field produced by an active NFC component in close proximity such as an active NFC component of computing device 200. While powered by an active NFC component, the passive NFC tag may read and write medication information to memory, transmit information to computing device 200, and optionally receive information from computing device 200. Such an exchange of information may be directed, for example, by a GUI of computing device 200 that instructs a patient to bring computing device 200 in close proximity to smart cap 100 when it is time to take medication.

Figure 3:
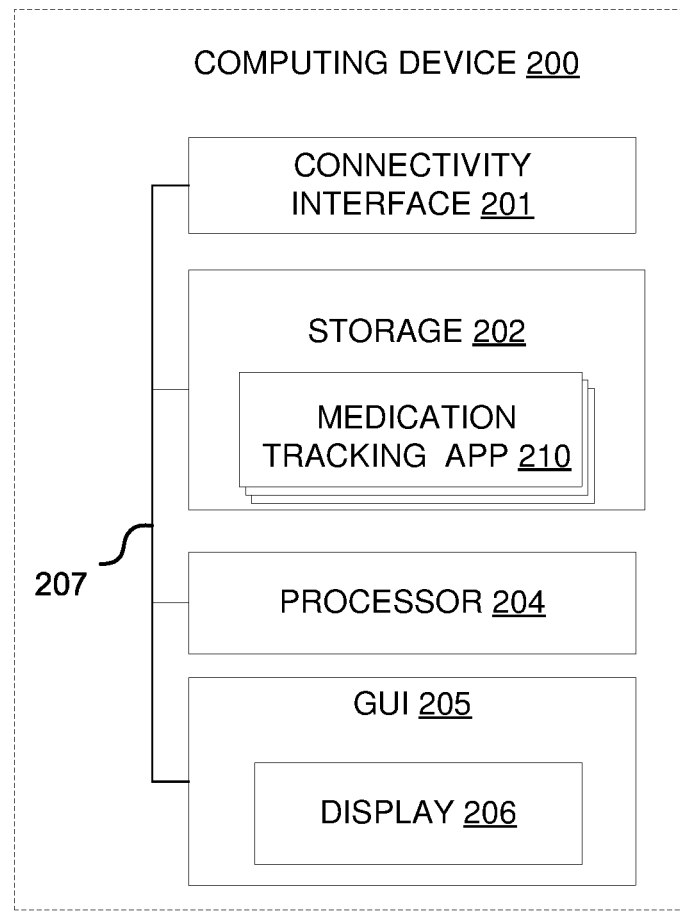
FIG. 3 is a block diagram illustrating a computing device, including a medication tracking application that may be used to interact with a smart cap and provide medication tracking in accordance with embodiments of the disclosed technology.

As one having skill in the art would appreciate from the above description, smart cap 100 in various embodiments may be configured to provide a low-cost, portable solution for medication tracking and compliance. In some embodiments this can be accomplished by leveraging the processing power of computing device 200 to provide medication tracking. FIG. 3 is a block diagram illustrating example components of one such computing device 200.

As illustrated in this example, computing device 200 comprises a connectivity interface 201, storage 202 with medication tracking application 210, processor 204, a graphical user interface (GUI) 205 including display 206, and a bus 207 for transferring data between the various components of computing device 200. In preferred embodiments, connectivity interface 201 connects computing device 200 to smart cap 100 through radio frequency communication (e.g., using NFC communication) or using Bluetooth LE communications. In alternative embodiments, connectivity interface 201 may communicate with smart cap 100 using Wi-Fi, a ZigBee network, a wireless local area network, a cellular network, or the like.

Storage 202 may comprise volatile memory (e.g. RAM), non-volatile memory (e.g. flash storage), or some combination thereof. In various embodiments, storage 202 may store medication tracking information received from smart cap 100. Additionally, storage 202 may store a medication tracking application 210, that when executed by processor 204, allows a patient to monitor their medication compliance history, receive medication reminders, process medication information received from smart cap 100, and transmit information to smart cap 100.

In various embodiments, a user may interact with activity tracking application 210 via a GUI 205 including a display 206, such as, for example, a touchscreen display that accepts various hand gestures as inputs. GUI 205 can also include a keypad, a microphone, or other input advices to accept additional forms of input from the user. In accordance with various embodiments, activity tracking application 210 may process medication information received from smart cap 100, transmit information to smart cap 100, allow a patient to interact with smart cap 100, and otherwise display information related to the patient's consumption of medication such as reports of the patient's compliance, the time of the next scheduled dosage, the number of medication units remaining in the medication container, the medication being taken, contact information for the pharmacy or prescribing doctor, drug interaction precaution information and other information.

For example, in one embodiment activity tracking application 210 may generate medication compliance alarms that notify the user when medications need to be taken by causing computing device 200 to display visual notifications and output audio notifications. In further embodiments, medication compliance alarms can further include other messages or alerts to the patient such as, for example, text messages to a device identified by the patient, alerts to a smart bracelet or other alert monitoring device worn by or kept in proximity with the patient. In implementations where computing device 200 includes an NFC module, the medication compliance alarms may be turned off by placing device 200 in close proximity to cap 100 (e.g., by touching the medication container with device 200). In such implementations, this action may additionally disable any medication compliance alarms generated by smart cap 100 as described above.

In another embodiment, activity tracking application 210 may help a patient locate a lost medication container. For example, a patient may use activity tracking application 210 to transmit a beacon from computing device 200 to smart cap 100 to locate smart cap 100. In response to the beacon, smart cap 100 may, for example, emit an audible alarm and/or flash an LED.

In embodiments, activity tracking application 210 may dynamically share medication related data with one or more secure servers including EMR databases and pharmacy databases such that medication related data is accessible by parties of interest including, for example, the patient, a doctor, the patient's caregiver, and pharmacies. In this manner, the patient's medication adherence may be improved, and doctors and EMRs may better treat the patient based on the patient's medication history.

In further embodiments, activity tracking application 210 may determine the number of medication units remaining in the medication container based on the weight information received from smart cap 100. In one such implementation, the remaining number of medication units may be determined by dividing the last recorded total weight of medication units by the known weight of each of the medication units. In another implementation, the remaining number of medication units may be determined by dividing the last recorded total weight of medication units by the last recorded change in weight of medication units after removing one or more units. The system can be programmed with the weight of the medication container and the portion of the smart cap supported by the weight sensor, so that this weight can be taken into account when determining the number of medication units remaining in the medication container. In other words, the weight of the medication container and portion of the cap supported by the weight sensor can be subtracted from the total weight to determine the weight of the medication units remaining in the container. In yet another implementation, the remaining number of medication units may be determined by tracking the total number of medication units, and deducting from this total each time a unit is removed based on a change in weight after the cap is removed.

As discussed above, the disclosed smart cap in various embodiments may include a weight sensor configured to provide absolute weight measurements, differential weight measurements, or both absolute and differential weight measurements of medication units in the medication container. Using these measurements, the number of medication units stored within the medication container may be determined and dynamically updated (e.g. using activity tracking application 210). Although weight sensor 104 is illustrated as a full bridge resistance sensor, other weight sensors, further described below, may be used. Although described as a weight sensor for simplicity, it should be noted that the weight sensor may alternatively or additionally function as a mass sensor that provides differential mass measurements and/or absolute mass measurements. In these implementations, a fixed gravity constant (e.g., standard acceleration due to gravity) or acceleration due to gravity detector can be used to convert the measured weight to mass.

In a first embodiment, the weight sensor measures changes in weight by determining the change in electrical resistance of a conductor load plate under pressure. In various implementations of this embodiment, the weight sensor may be implemented as a strain gauge, including strain gauge load cells and resistive wire that are connected to a load plate in various configurations such as, for example, a spiral pattern, a zigzag pattern, etc.

As pressure on the load plate increases or decreases by adding or removing medication units, the load plate displaces a distance corresponding to the pressure, thereby reducing or increasing the conductor's cross-sectional area. In other words, the strain (deformation due to applied pressure) on the conductor changes in response to changes in load pressure, or weight. A reduction in the cross sectional area of the conductor will increase electrical resistance. Conversely, an increase in the cross-sectional area of the conductor will decrease resistance. In various implementations, the change in resistance may be measured using one or more resistance detection circuits such as, for example, Wheatstone bridges, differential amplifiers, instrumentation amplifiers, and other tools known to those having skill in the art.

In a second embodiment, the weight sensor is a piezo-based weight sensor that functions by measuring the change in capacitance of a piezoelectric crystal under pressure. In various implementations of these embodiments, a piezocrystal is disposed between two conductive electrodes, where one of the electrodes is fixed while the other is mechanically connected to a load plate or acts as the load plate itself.

As medication units are added, the pressure on the load plate increases and the load place is displaced by a corresponding amount that causes compression of the piezoelectric crystal. This compression decreases the physical distance between the plates, which causes a change in the overall capacitance value of the crystal sensor that can be measured. Several methods may be used to measure this change in capacitance such as, for example, methods using AC Wheatstone bridges, charge and discharge timing, and other methods known to those having skill in the art.

In a third embodiment, the weight sensor is a quantum tunneling compound (QTC) sensor that functions by measuring the change in resistance of a QTC material under pressure. In various implementations, sheets of QTC material, QTC pills, or QTC cable may be employed in the weight sensor. In yet further implementations, other QTC configurations may be employed.

In one example implementation, a QTC sheet is positioned between two electrodes and a load plate mechanically attached to one of the electrodes. As medication units are added to the medication container, the pressure on the load plate increases, causing it to displace by a corresponding amount. Subsequently, the quantum tunneling effect of the QTC substance will increase, causing an increase in current flow. In various implementations, the change in current flow may be measured using one or more of differential amplifiers, instrumentation amplifiers, and other tools known to those having skill in the art.

In a fourth embodiment, the weight sensor is a capacitance-based weight sensor that functions by measuring the change in capacitance between two conductive plates that are physically separated. In various implementations of this embodiment, the weight sensor includes two conductive electrodes spaced by a dielectric or air, whereby one of the electrodes is fixed and the other electrode is mechanically coupled to a load plate or acts as a load plate. As medication units are added to the medication container, the pressure on the load plate increases, causing it to displace by a corresponding amount, thereby causing the load plate electrode to compress and distort. As this compression decreases the physical distance between the plates, the capacitance changes. The reduction in distance reduces the overall capacitance of the sensor and can be measured using various methods such as methods that use AC Wheatstone bridges, charge timing, discharge timing, and other methods known to those having skill in the art.

In a fifth embodiment, the weight sensor is an inductance-based weight sensor that functions by measuring the change in inductance of an inductor. In various implementations of this embodiment, a spring-type inductor placed under pressure or a ferrous core going into or out of an inductor may be used. Generally, the inductor will be connected to a load plate.

As medication units are added to the medication container, the pressure on the load plate increases, causing it to deflect by a corresponding amount that causes the load plate to compress and distort. This compression of the inductor causes a change in the inductance, which may be measured to determine the weight of the medication units in the medication container. The change in inductance may be measured using various methods such as methods that use AC Wheatstone bridges, charge timing, discharge timing, and other methods known to those having skill in the art.

Because high humidity can cause moisture vapor to be absorbed by many substances, this may influence the measured weight of the medication units. Accordingly, in further embodiments of the smart cap's weight measuring apparatus, the humidity of the medication container, external environment, or both may be accounted for in determining the number of medication units in the container. In one such example, one or more humidity sensors in the smart cap or medications container may measure the humidity to compensate for weight measurement errors due to humidity, or due to humidity levels over time. In yet further embodiments, a temperature sensor may measure temperature and compensate for temperature-induced changes in weight using techniques known to those having skill in the art.

Figure 4:
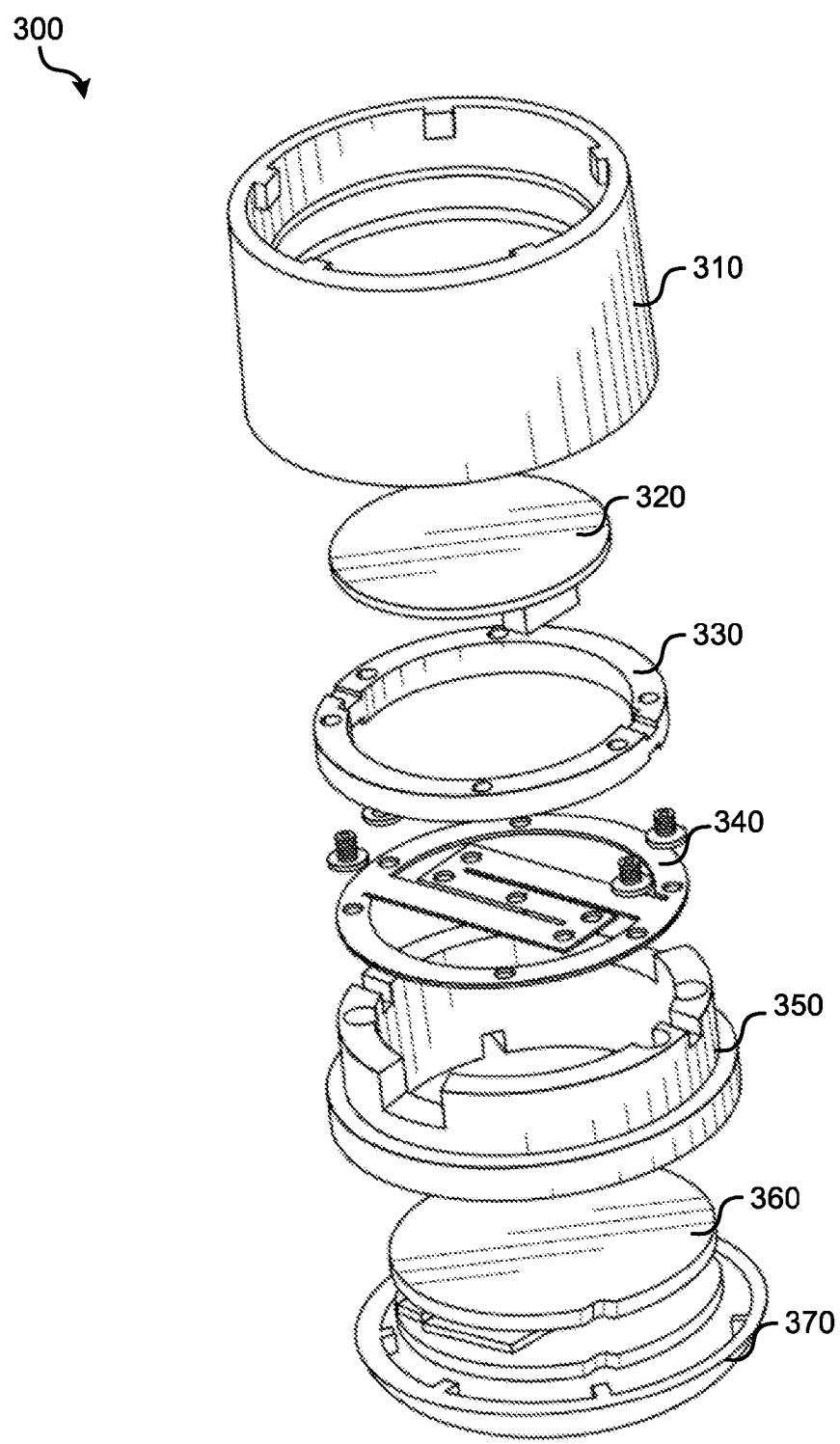
FIG. 4 is a diagram showing an exploded view of components of a smart cap that uses an example strain gauge load cell to make weight measurements of medication units in accordance with embodiments.

FIG. 4 is a diagram showing an exploded view of components of a smart cap 300 that uses an example strain gauge load cell to make weight measurements of medication units in accordance with embodiments. Smart cap assembly 300 includes an enclosure and cover 310, a platform 320 for placing medication units, a support ring 330, a load cell 340, a support 350, a printed circuit board 360, and a cap 370. FIG. 4 is described in conjunction with FIG. 5, which is a diagram showing a partially assembled smart cap, including an assembled weight sensor, including strain gauges 342 electrically coupled to printed circuit board 360.

During weight measuring operations, a user may place the smart cap upside down (i.e., with cap 370 facing down) on a surface and mount medication units on platform 320. As pressure on platform 320 increases, platform 320 displaces downward and pushes on load cell 340, which, as further described below, causes deformation of beams or spring elements on load cell 340. Strain gauges 342 mounted on the beams of load cell 340 measure the distortion or strain on the beams, and output electrical signals that may be used to determine the total load or weight of the medication units based on the measured strain.

Strain gauges 342 include at least one strain gauge that measures strain (i.e., elongation or contraction) as a change in electrical resistance caused by tension or compression of the beams of the load cell, and preferably, at least one strain gauge that is in tension and one strain gauge that is in compression. For example, strain gauges 342 may be arranged in a quarter bridge configuration, half bridge configuration, or Wheatstone bridge configuration.

Figure 5:
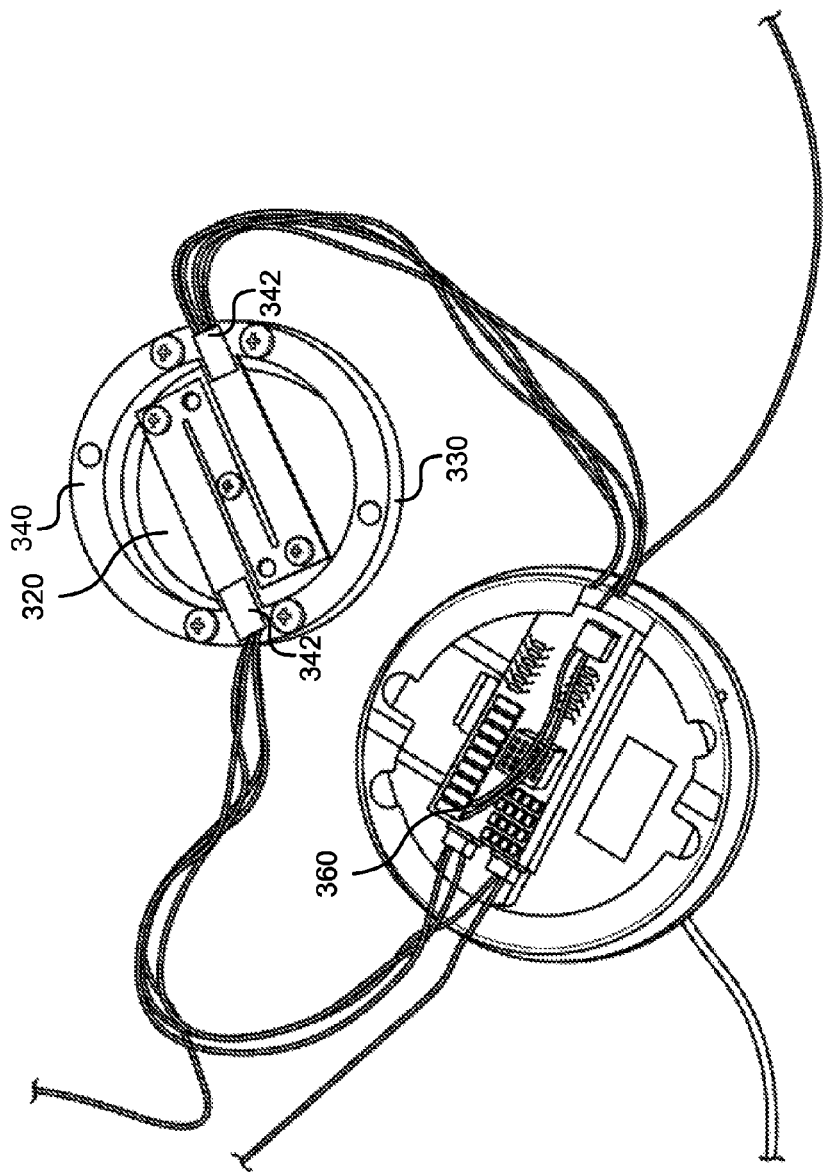
FIG. 5 is a diagram showing the partially assembled smart cap of FIG. 4, including an assembled weight sensor, in accordance with embodiments.

In the particular example of FIG. 5, load cell 340 is mounted with two strain gauges on a top surface of its beams (e.g., in tension) and with two strain gauges (not shown) on an opposite bottom surface of the beam (e.g., in compression). These four strain gauges may form a Wheatstone bridge that maximizes the sensitivity of the load cell. As would be appreciated by one having skill in the art, load cell 340 may be mounted with any number of strain gauges subject to the available mounting space on load cell 340.

Figure 6:
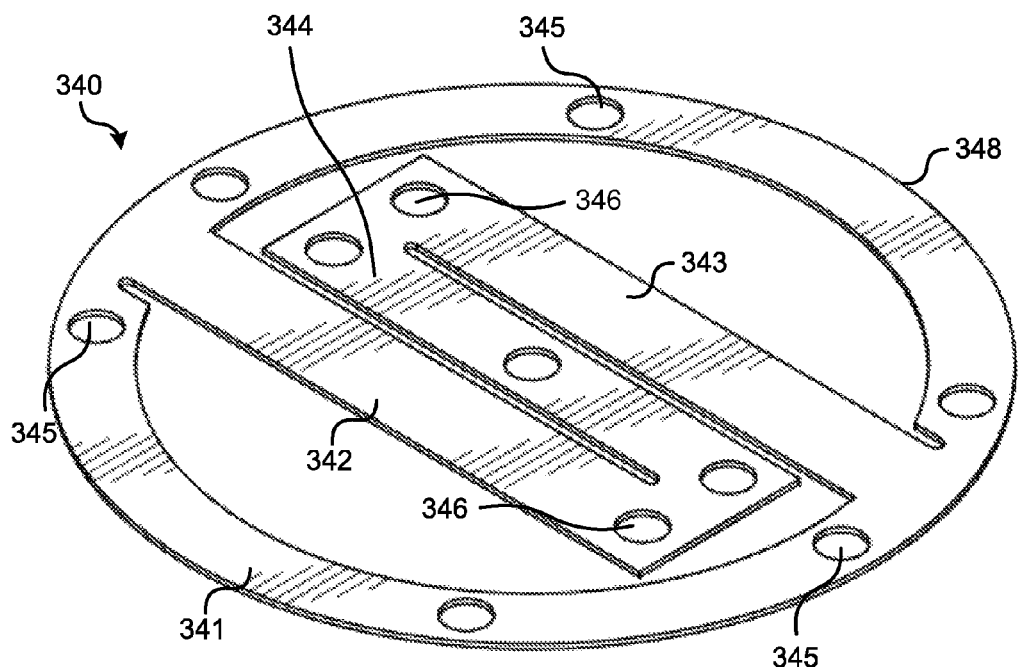
FIG. 6 illustrates an exemplary design of a strain gauge load cell in accordance with embodiments.

FIG. 6 illustrates an exemplary double cantilever beam design for a load cell 340 in accordance with embodiments. In various implementations, load cell 340 may be dimensioned to fit in a smart cap or other device having a circular housing. As shown in this embodiment, load cell 340 includes a ring or annular portion 348, two parallel spring elements or beams 342 and 343 extending inward from annular portion 348, and a center connecting beam 344 that couples beam 342 and 343. In embodiments, load cell 340 may have an outer diameter of less than 45 millimeters (e.g., 38.1 millimeters) and may comprise a suitable metal or other material (e.g., aluminum) that may be made stiff in an off-axis direction of load cell 340. In embodiments, load cell 340 is made of a flat piece of material (e.g., aluminum) having an outer diameter (i.e., outer diameter of annular portion 348) that is at least two orders of magnitude greater than its thickness. In particular embodiments, load cell 340 has an outer diameter of between 30 and 45 millimeters.

Annular portion 348 may provide structural integrity to load cell 340 and comprises a plurality of holes 345 for mounting load cell 340 to support ring 330 using a suitable fastening mechanism (e.g., screws, pins, nails, etc.). Alternatively, in other embodiments, annular portion 348 may be attached to support ring 330 using other suitable attachment means, such as, for example, by gluing or welding.

In this embodiment, outer beams 342-343 are fixed to annular portion 348 on one end and coupled by a center connecting beam 344 on the other end. Beams 342-343 and 344 include a plurality of holes 346 for mounting and fixing load cell beams 342-343 and 344 to platform 320 using a suitable attachment mechanism (e.g., screws, pins, nails, etc.). In embodiments, mounting holes 346 may be placed in a configuration that provides linear travel up and down and prevents tilting of platform 320 as it displaces from the weight of medication units.

As illustrated in the above embodiments, center connecting beam 344 keeps the distance between beams 342 and 343 fixed relative to each other as beams 342 and 343 deform in response to pressure from the displacing platform 320. In alternative embodiments, center connecting beam 344 may be omitted and beams 342 and 343 may each have one end fixed to annular portion 348 and another end floating over the center aperture of load cell 340.

During construction of the weight sensor, at least one strain gauge may be mounted and bonded on each deforming beam 342-343 of load cell 340. For example, as illustrated by the implementation of FIG. 5, a strain gauge in tension may be mounted on a top surface of each beam 342-343, and a strain gauge in compression may be mounted on the bottom surface of each beam 342-343.

The thickness of beams 342 and 343, in various embodiments, is at least ten times less than the width of the beams, and least one hundred times greater than the diameter of load cell 340. For example, in particular embodiments, beams 342 and 343 may be between 0.2 and 0.3 millimeters thick and between 3.5 and 5.5 millimeters wide. In particular embodiments, center connecting beam 344 may be between 3.0 and 4.5 millimeters wide. This flat beam design may help increase the amount of deflection experienced by beams 342-343 under deflection by platform 320, thereby increasing the measured beam strain by the strain gauges. Such a design may be particularly helpful for measuring small changes in weight (e.g., medication units weighing 1 to 10 mg).

As decreasing the thickness of beams 342 and 343 may increase the off-center or off-axis sensitivity (i.e., measurement error) of the load cell, particularly when weight is loaded on the edge of platform 320, in various embodiments beams 342 and 343 may be made stiff in the off-axis direction. For example, the beam may be 100 times stiffer in the off-axis direction relative to the on-axis direction. Accordingly, the measurement error of the signal output by the strain gauges may be 100 times less than the signal itself. For example, if a 10 mg pill is weighed, the error would be about 0.1 mg or less. In particular embodiments, the off-axis spring constant of beams 342-343 may be between 150 and 300 N/m.

Figure 7:
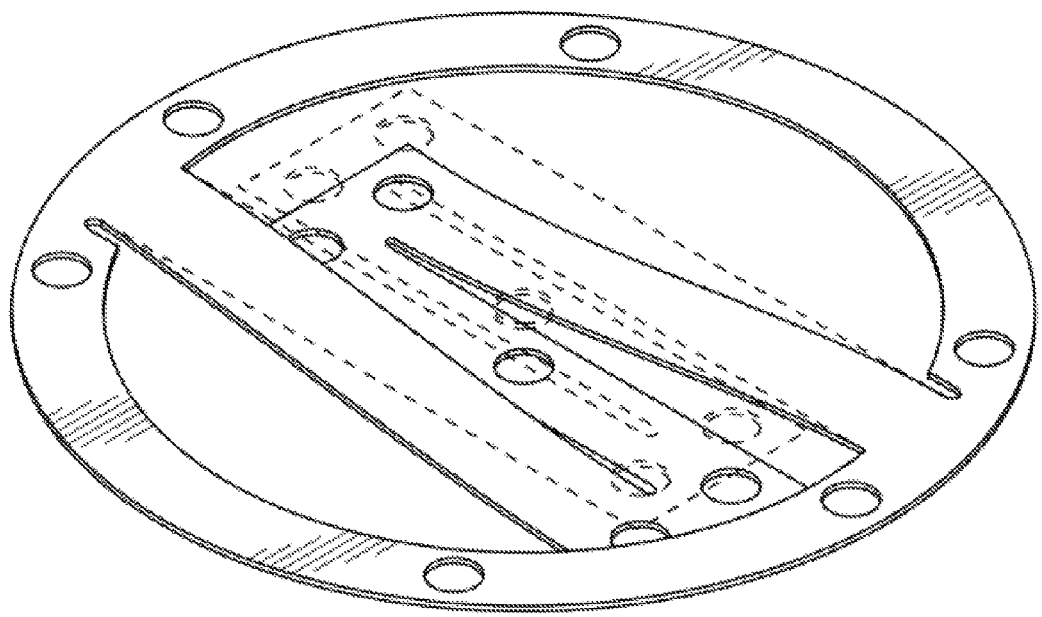
FIG. 7 illustrates the load cell of FIG. 6 after the load cells beams deform in response to an applied force by a platform.

As platform 320 displaces downward, beams 342-343 deform along the ends that are not fixed to annular portion 348. FIG. 7 illustrates deformed beams 342 and 343 in accordance with an embodiment. The illustrated two beam design, with one side of each beam fixed to annular portion 348, and the other side coupled to center beam 344, may act as a Roberval mechanism that prevents tilting of platform 320 as it pushes downward on load cell 340. For example, if a user of the smart cap places medication units on the edge of platform 320 as opposed to its center, the platform 320 may still travel downward in a linear direction without any noticeable tilt.

Figure 8A:
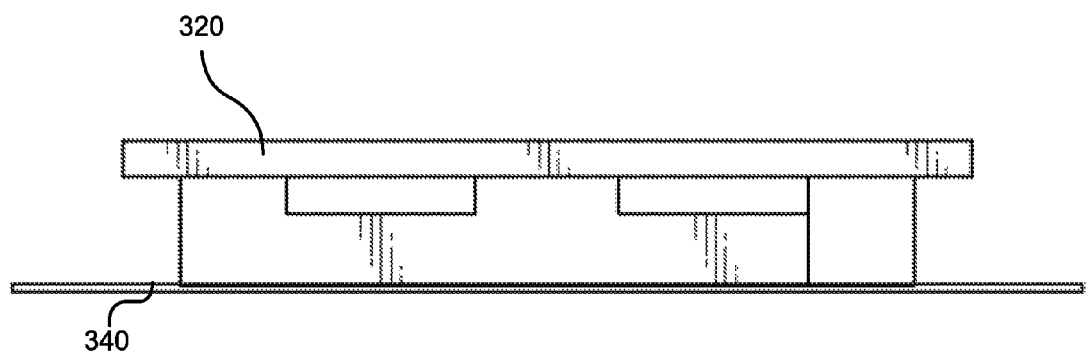
FIG. 8A is an example model of a weight sensor assembly including a platform and load cell before displacement of the platform, in accordance with embodiments.
Figure 8B:
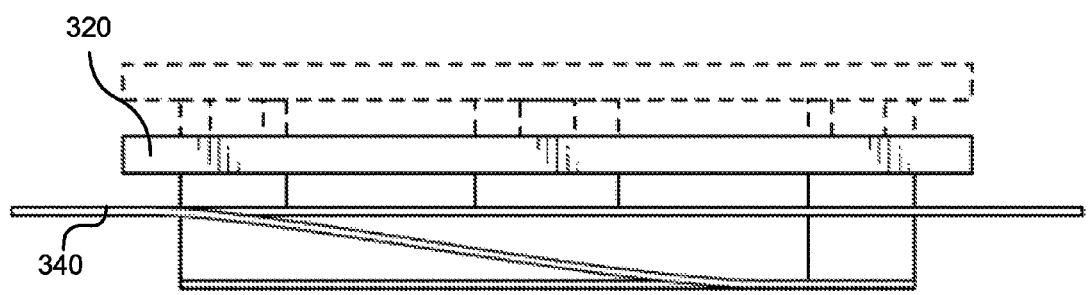
FIG. 8B is an example model of a weight sensor assembly including a platform and load cell after displacement of the platform, in accordance with embodiments.

FIGS. 8A-8B illustrate an example model of a weight sensor assembly including a platform 320 and load cell 340, before and after the downward displacement of platform 320. As shown in FIG. 8B, the double cantilever beam design of load cell 340 allows platform 320 to travel downward in an approximately linear direction without any perceptible tilt.

Although load cell 340 has been described above with reference to an example double cantilever beam design, load cell 340 need not be limited to this precise configuration in accordance with embodiments of the technology disclosed herein. For example, the beams need not necessarily extend at right angles from the annular portion. Additionally, a different number of beams or configuration of beams may be used. For example, the beams (e.g., three beams) may be arranged in a spiral configuration with the platform attached to the center of the load cell.

Figure 9:
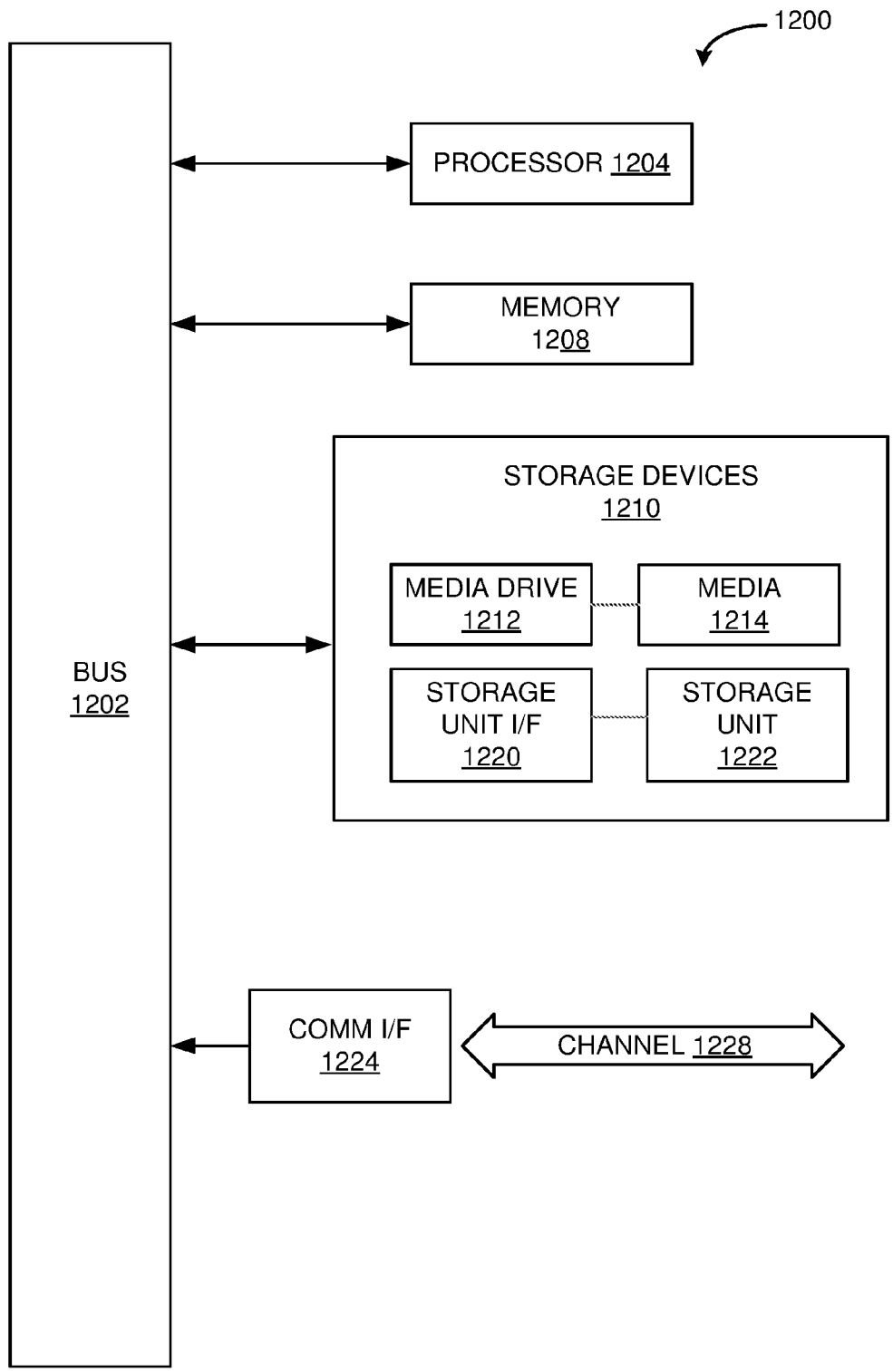
FIG. 9 illustrates an example computing module that may be used in implementing features of various embodiments of the disclosed technology.

FIG. 9 illustrates an example computing module that may be used in implementing features of various embodiments of the disclosed technology. As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 9. Various embodiments are described in terms of this example-computing module 1200. After reading this description, it will become apparent to a person skilled in the relevant art how to implement the application using other computing modules or architectures.

Referring now to FIG. 9, computing module 1200 may represent, for example, computing or processing capabilities found within desktop, laptop, notebook, and tablet computers; hand-held computing devices (tablets, PDA's, smart phones, cell phones, palmtops, etc.); wearable computing devices such as smartwatches; mainframes, supercomputers, workstations or servers; or any other type of special-purpose or general-purpose computing devices as may be desirable or appropriate for a given application or environment. Computing module 1200 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 1200 might include, for example, one or more processors, controllers, control modules, or other processing devices, such as a processor 1204. Processor 1204 might be implemented using a general-purpose or special-purpose processing engine such as, for example, a microprocessor, controller, or other control logic. In the illustrated example, processor 1204 is connected to a bus 1202, although any communication medium can be used to facilitate interaction with other components of computing module 1200 or to communicate externally.

Computing module 1200 might also include one or more memory modules, simply referred to herein as main memory 1208. For example, preferably random access memory (RAM) or other dynamic memory, might be used for storing information and instructions to be executed by processor 1204. Main memory 1208 might also be used for storing temporary variables or other intermediate information during execution of instructions to be executed by processor 1204. Computing module 1200 might likewise include a read only memory ("ROM") or other static storage device coupled to bus 1202 for storing static information and instructions for processor 1204.

The computing module 1200 might also include one or more various forms of information storage mechanism 1210, which might include, for example, a media drive 1212 and a storage unit interface 1220. The media drive 1212 might include a drive or other mechanism to support fixed or removable storage media 1214. For example, a hard disk drive, a solid state drive, a magnetic tape drive, an optical disk drive, a CD, DVD, or Blu-ray drive (R or RW), or other removable or fixed media drive might be provided. Accordingly, storage media 1214 might include, for example, a hard disk, a solid state drive, magnetic tape, cartridge, optical disk, a CD, DVD, Blu-ray or other fixed or removable medium that is read by, written to or accessed by media drive 1212. As these examples illustrate, the storage media 1214 can include a computer usable storage medium having stored therein computer software or data.

In alternative embodiments, information storage mechanism 1210 might include other similar instrumentalities for allowing computer programs or other instructions or data to be loaded into computing module 1200. Such instrumentalities might include, for example, a fixed or removable storage unit 1222 and an interface 1220. Examples of such storage units 1222 and interfaces 1220 can include a program cartridge and cartridge interface, a removable memory (for example, a flash memory or other removable memory module) and memory slot, a PCMCIA slot and card, and other fixed or removable storage units 1222 and interfaces 1220 that allow software and data to be transferred from the storage unit 1222 to computing module 1200.

Computing module 1200 might also include a communications interface 1224. Communications interface 1224 might be used to allow software and data to be transferred between computing module 1200 and external devices. Examples of communications interface 1224 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1224 might typically be carried on signals, which can be electronic, electromagnetic (which includes optical) or other signals capable of being exchanged by a given communications interface 1224. These signals might be provided to communications interface 1224 via a channel 1228. This channel 1228 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 1208, storage unit 1220, media 1214, and channel 1228. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 1200 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

What is claimed is:

1. A cap for a medication container, comprising:
    a circuit board;
    a weight sensor electrically coupled to the circuit board and configured to generate electrical input signals representative of a total weight of medication units in the medication container;
    a processor electrically coupled to the circuit board and configured to process the electrical input signals generated by the weight sensor;
    a memory configured to store medication information associated with medication in the medication container, wherein the medication information comprises the processed electrical input signals generated by the weight sensor;
    a wireless transmitter configured to transmit the stored medication information to a computing device communicatively coupled to the cap;
    an RFID tag comprising a near field communication (NFC) tag; and
    a lock, wherein the cap may be unlocked by bringing a near field communication interface of the computing device in close proximity to the NFC tag of the cap,
    wherein in response to the computing device communicatively coupling to the cap, the processor is configured to store in the memory an identification of the computing device, and the time the cap and computing device communicatively coupled.

2. The cap of claim 1, further comprising an enclosure, wherein the enclosure houses the circuit board, weight sensor, processor and wireless transmitter.

3. The cap of claim 2, further comprising a cover releasably attached to the enclosure, wherein the enclosure is disposed within the cover.

4. The cap of claim 1, wherein the wireless transmitter is a Bluetooth low energy (LE) transmitter.

5. The cap of claim 1, wherein the RFID tag comprises the wireless transmitter and the memory.

6. The cap of claim 1, wherein the weight sensor comprises a strain gauge configured to measure the change in resistance of a conductor when medication units are inserted into or removed from the medication container.

7. The cap of claim 1, further comprising an accelerometer configured to generate electrical input signals representative of the position of the cap.

8. The cap of claim 1, further comprising an audible or visual indicator device configured to alert a user of a medication dosing time, wherein the medication information comprises the medication dosing time, and wherein the processor is configured to activate the indicator device at the dosing time.

9. The cap of claim 8, wherein the processor is configured to:
determine a change in the total weight of the medication units in the medication container after the dosing time based on electrical signals generated by the weight sensor; and
turn off the indicator if it is determined that the change in the total weight after the dosing time matches a predetermined amount.

10. The cap of claim 9, wherein the processor is configured to generate an alert if it is determined that the change in the total weight does not match the predetermined amount.

11. The cap of claim 8, wherein the transmitter is a transceiver configured to receive information signals from the computing device, and wherein in response to receiving a beacon signal from the computing device attempting to locate the cap, the processor is configured to activate the indicator device.

12. The cap of claim 6, wherein the cap comprises a platform and a load cell, wherein the load cell comprises an annular portion and a beam extending inwardly from the annular portion, wherein the strain gauge is mounted on the beam.

13. A cap for a medication container, comprising:
a cover;
an enclosure attached to the cover, wherein the enclosure is disposed within the cover and is configured to seal the opening of the medication container;
a circuit board; and
a weight sensor assembly electrically coupled to the circuit board and configured to generate electrical input signals representative of the total weight of the medication container, wherein the weight sensor assembly comprises:
a platform;
a load cell comprising an annular portion and a beam coupled to the platform, wherein the beam comprises a first end fixed to the annular portion and a second end that deforms as the platform displaces downward in response to an applied force; and
a strain gauge mounted on the beam, wherein the strain gauge is electrically coupled to the circuit board,
wherein the enclosure houses the circuit board and the weight sensor assembly.

14. The cap of claim 13, further comprising an accelerometer configured to generate electrical input signals representative of the position of the cap.

15. The cap of claim 14, further comprising a processing module configured to process the electrical input signals generated by the weight sensor and the accelerometer, and determine a total weight of the medicament container, including medicament units, based on the processed signals.

16. The cap of claim 15, further comprising: a wireless transmitter configured to transmit the total weight of the medicament container to a computing device communicatively coupled to the cap.

17. The cap of claim 16, further comprising an RFID tag, wherein the RFID tag comprises the wireless transmitter and the memory.

18. The cap of claim 14, further comprising a processing module configured to process the electrical input signals generated by the weight sensor assembly and the accelerometer, and determine a current number of medicament units in the medicament container based on the processed signals.

19. The cap of claim 18, wherein the processing module comprises a memory that stores: the weight or mass of the medicament container without any of the medicament units; the weight or mass of one of the medicament units; and the current number of medicament units in the medicament container.

* * * * *